US009181517B1

(12) United States Patent
Takeuchi

(10) Patent No.: US 9,181,517 B1
(45) Date of Patent: Nov. 10, 2015

(54) COMPOSITION FOR TREATING CONTACT LENSES WITH AN AQUEOUS SOLUTION RESULTING IN VISIBLE PROTEIN REMOVAL

(71) Applicant: TTE international Inc., Torrance, CA (US)

(72) Inventor: Satoshi Takeuchi, Torrance, CA (US)

( * ) Notice: Subject to any disclaimer, the term of this patent is extended or adjusted under 35 U.S.C. 154(b) by 0 days.

(21) Appl. No.: 14/464,651

(22) Filed: Aug. 20, 2014

Related U.S. Application Data

(60) Provisional application No. 61/959,341, filed on Aug. 20, 2013.

(51) Int. Cl.

| | |
|---|---|
| ***A61L 2/00*** | (2006.01) |
| ***G02C 13/00*** | (2006.01) |
| ***C11D 11/00*** | (2006.01) |
| ***C11D 7/32*** | (2006.01) |
| ***C11D 7/26*** | (2006.01) |

(52) U.S. Cl.
CPC ............ *C11D 11/0017* (2013.01); *C11D 7/261* (2013.01); *C11D 7/3281* (2013.01)

(58) Field of Classification Search
CPC .... C11D 3/0078; C11D 3/361; C11D 3/3753; C11D 9/225; A61L 2/00; G02C 13/00
See application file for complete search history.

(56) References Cited

U.S. PATENT DOCUMENTS

| | | | | |
|---|---|---|---|---|
| 4,120,949 | A * | 10/1978 | Bapatla et al. | 424/78.04 |
| 4,560,491 | A * | 12/1985 | Sherman | 514/275 |
| 5,141,665 | A * | 8/1992 | Sherman | 514/566 |
| 5,858,937 | A * | 1/1999 | Richard et al. | 510/112 |
| 6,369,112 | B1 * | 4/2002 | Xia | 514/635 |
| 2003/0021829 | A1 * | 1/2003 | Hamano et al. | 424/429 |
| 2011/0070306 | A1 * | 3/2011 | Baker et al. | 424/484 |
| 2014/0322193 | A1 * | 10/2014 | Kaleko | 424/94.6 |

* cited by examiner

*Primary Examiner* — Charles Boyer
(74) *Attorney, Agent, or Firm* — Michael D. Eisenberg

(57) ABSTRACT

A composition for cleaning contact lenses and producing a removable visible discharge comprising: polyvinyl-alcohol; povidone; and an isotonic contact solution.

4 Claims, 1 Drawing Sheet

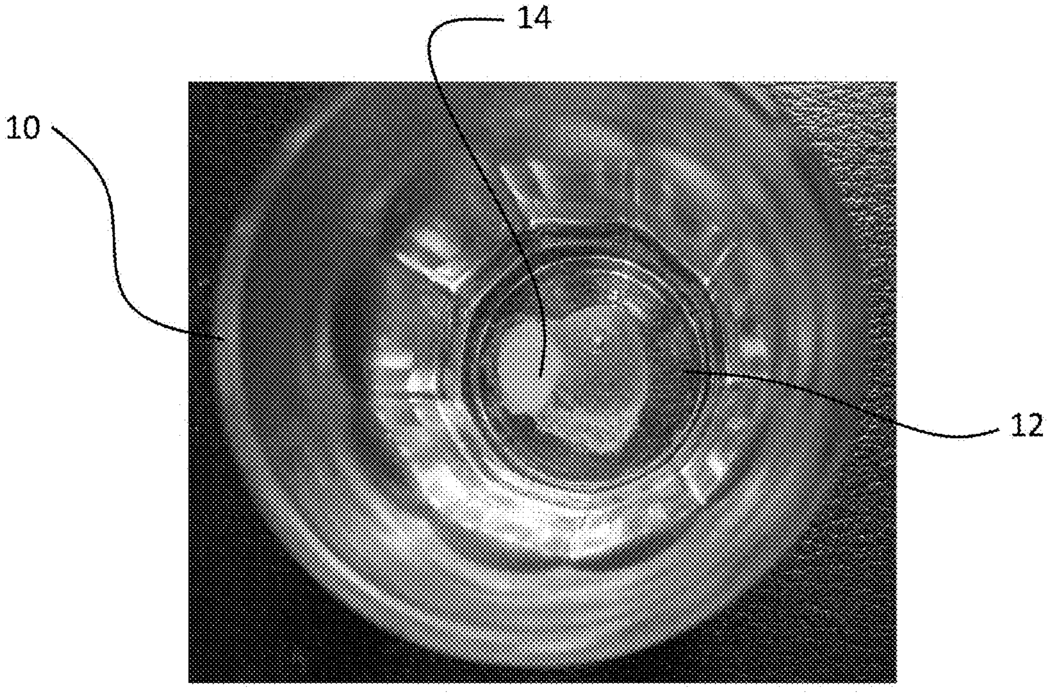
14
10
12

COMPOSITION FOR TREATING CONTACT LENSES WITH AN AQUEOUS SOLUTION RESULTING IN VISIBLE PROTEIN REMOVAL

TECHNICAL FIELD

The present invention, in some embodiments thereof, relates to contact lenses cleaners and compositions thereof. Specifically it relates to an aqueous solution that cleans and disinfects contact lenses while producing visible protein discharge.

BACKGROUND OF THE INVENTION

Contact lenses are worn for a variety reasons ranging from medical to aesthetic. Contacts come into direct contact with the cornea and must be kept clean for continued use and to prevent infection. Failure to keep contact lenses properly cleaned can result in irritation, infection, and lasting damage to a user's eyes including vision loss and blindness.

Cleaning solution is used to clean contacts, an example of which is U.S. Pat. No. 5,858,937, "Treatment of contact lenses with aqueous solution including phosphonic compounds". U.S. Pat. No. 5,858,937 is incorporated by reference in its entirety in this application. Failure to keep contact lenses properly cleaned can occur from failure to clean or failure to properly use cleaning solution. One manner in which people fail to properly use cleaning solution is through failure to understand the purpose of different solutions. Contact solutions include: cleaning solution, rinsing solution, disinfecting solution, multipurpose solution, and rewetting solution. These perform different purposes and are not equally beneficial at removing protein build up. Even a once effective solutions may become ineffective overtime. Factors such as heat can alter the efficacy of the solution over time regardless of an expiration date.

BRIEF SUMMARY OF EMBODIMENTS OF THE INVENTION

Current contact lens cleaners and solutions produce no evidence or confirmation that they are working for a user. The solutions and protein discharge are both clear. The user has no visible confirmation and must rely on the solution working properly. This depends on the user relying on their understanding of the product and proper usage as well as on manufacture expiration dates, which, as previously discussed, may not accurately reflect any individual bottles efficacy depending on circumstances.

There is therefore a need for a contact solution that provides a visible confirmation for the user that the solution is working, that a user's lenses are protein free, and that none of the discharge is on the lens and in need of further rinsing.

The present invention in some embodiments thereof, relates to contact lenses cleaners and compositions thereof. Specifically it relates to an aqueous solution that cleans and disinfects contact lenses while producing visible protein discharge.

Aspects of some embodiments of the present invention include a composition for cleaning contact lenses and producing visible discharge. The composition comprises polyvinyl-alcohol, povidone, and an isotonic contact solution.

Aspects of a further embodiment of the present composition may contain about 0.1% to 1% polyvinyl-alcohol and 0.1% to 1% povidone. The total volume of the povidone and polyvinyl alcohol aqueous solution is about 0.25-0.5 ml. The povidone and polyvinyl alcohol aqueous solution will additionally be added to about 5-10 ml contact solution. The overall volume may change in other embodiments, and the ratios of the component parts may increase proportionately.

In another embodiment the isotonic solution may be a specific type of solution. The solution may comprise a phosphonic compound represented by the formula:

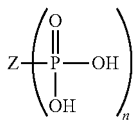

wherein Z is a connecting radical equal in valence to n, wherein n is an integer from 1 to 6, and containing 1 to 12 carbon atoms, and wherein Z is selected from the group consisting of unsubstituted or substituted saturated hydrocarbon radicals and amine-containing radicals, which amine-containing radicals are saturated hydrocarbon radicals in which the carbon atoms are interrupted with at least one nitrogen atom that forms a secondary or tertiary amine and in which the number of carbon atoms in the amine containing radical is at least n+1, wherein said substituted saturated hydrocarbon radicals may be substituted with halogen, hydroxy, amine, carboxy, alkylcarbonyl, alkoxycarbonyl and/or substituted or unsubstituted phenyl, wherein the substituted phenyl may be substituted with halogen, hydroxy, amine, carboxy and/or alkyl, and wherein said alkyl or alkoxy has 1 to 4 carbon atoms, and an effective amount of at least one non-oxidative antimicrobial agent for a contact-lens treating solution.

In yet another embodiment of the composition the isotonic solution comprises (in percent by weight volume): polyhexamethylenebiguanide HCl (as a 20% w/w solution available under themark Cosmocil CQ, from ICI ChemicalCo.) 0.00047, boric acid 0.64, sodium borate 0.12, edetate disodium 0.11, sodium chloride 0.49, poloxamine (Tetronic® 1107 from BASF Co.) 1.00, tetrasodium etidronate (as a 30% (w/w) solution available under the markDeQuest® 2016 from Monsanto Co.), hydrochloride acid 1N as required for pH adjustment, sodium hydroxide 1N as required for pH adjustment, and purified water up to 100.

This embodiment may additionally have added sterile water, citrus acid, gluconic acid, tartanic acid, potassium citrate, and carbonate sodium as needed to increase efficacy of the solution.

Another embodiment of the invention includes a method for cleaning contact lenses and producing visible discharge comprising the application of a composition comprises polyvinyl-alcohol, povidone, and an isotonic contact solution to contact lenses in a container.

A number of contact solutions may be used as a base. In one embodiment a sterile isotonic solution is used. Sterile isotonic solutions both clean and disinfect. By adding about 0.1%-1% polyvinyl-alcohol and povidone the protein discharge becomes opaque as a visible white discharge.

Many users find multipurpose solutions, such as the described isotonic solution, to be beneficial in their cleaning processes. However, the type of solution can depend on any specific user's need or preference.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

FIG. 1 is a visual depicting the effects of an embodiment of the invention.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

An aspect of some embodiments of the present invention relates to contact lenses cleaners and compositions thereof. Specifically it relates to an aqueous solution that cleans and disinfects contact lenses while producing visible protein discharge.

FIG. 1 is a visual depicting the effects of an embodiment of the invention. In a container 10 the composition of the present invention 12 results in and solid opaque mass 14. The solid opaque mass 14 is composed of protein discharge and dirt from the contact. Protein discharge and dirt originate from the eye and the environment respectively. The solid opaque mass 14 is removable. After removal of the opaque mass 14, additional polyvinyl alcohol and povidone may be added directly to the remaining composition of the present invention 12 for reuse. In a non-limiting embodiment of the present invention, the reaction forming the solid opaque mass 14 takes six hours to complete. The reaction time depends on the concentration of povidone and polyvinyl alcohol used with the rate increasing with the concentration.

The composition of the present invention in one embodiment includes about 0.25 ml to 0.5 ml combined: about 0.1-1% povidone and about 0.1-1% polyvinyl-alcohol, and about 5-10 ml contact solution. Greater volumes may be used in similar ratios. In a non-limiting embodiment the concentration of the povidone-polyvinyl alcohol saline solution, which is add to the isotonic contact solution, contains 0.55% povidone and 0.55% polyvinyl alcohol.

Polyvinyl-alcohol is a water soluble synthetic polymer with the chemical formula $[CH_2CH(OH)]_n$. As a polymer polyvinyl-alcohol can be formed as a solid, but as it is water soluble it can be in solution as well. In solution it is considered a safe substance in interactions with the human eye.

Povidone is a synthetic water soluble polymer that is sometimes referred to as polyvinylpyrrolidone, PVP, or polyvidone. Povidone is regularly used safely in a variety of pharmaceutical uses and has been approved by the FDA.

Both povidone and polyvinyl readily form films.

Povidone and polyvinyl may be used in conjunction with a variety of solutions. Contact solutions vary for many reasons ranging from an overall purpose, as described above, or for targeted treatments such as dry or sensitive eyes. Generally a contact solution will be a sterile saline solution containing buffers that help protect your eyes, and other agents to help keep the liquid sterile. The solution described in U.S. Pat. No. 5,858,937 describes a commonly used contact solution and is a non-limiting example of what may be used as a contact solution by a user. Other contact solutions may be used.

In one embodiment of the invention povidone and polyvinyl are used in conjunction with an isotonic solution that contains: polyhexamethylenebiguanide HCL; boric acid; sodium borate; edate disodium; sodium chloride; poloxamine; tetrasodium etidronate; and hydrochloride acid. In another embodiment sterile water; citrus acid; gluconic acid; tartanic acid; potassium citrate; and carbonate sodium are also included.

The above use of polyvinyl-alcohol and povidone are not exclusive of other uses.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A composition for cleaning contact lenses and producing visible discharge, the composition comprising:

polyvinyl-alcohol;

povidone; and an isotonic contact solution, comprising a phosphonic compound represented by the formula:

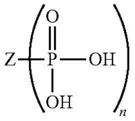

wherein Z is a connecting radical equal in valence to n, wherein n is an integer from 1 to 6, and containing 1 to 12 carbon atoms, and wherein Z is selected from the group consisting of unsubstituted or substituted saturated hydrocarbon radicals and amine-containing radicals, which amine-containing radicals are saturated hydrocarbon radicals in which the carbon atoms are interrupted with at least one nitrogen atom that forms a secondary or tertiary amine and in which the number of carbon atoms in the amine containing radical is at least n+1, wherein said substituted saturated hydrocarbon radicals may be substituted with halogen, hydroxy, amine, carboxy, alkylcarbonyl, alkoxycarbonyl and/or substituted or unsubstituted phenyl, wherein the substituted phenyl may be substituted with halogen, hydroxy, amine, carboxy and/or alkyl, and wherein said alkyl or alkoxy has 1 to 4 carbon atoms, and an effective amount of at least one non-oxidative antimicrobial agent for a contact-lens treating solution.

2. A composition for cleaning contact lenses and producing visible discharge, the composition comprising:

polyvinyl-alcohol;

povidone; and an isotonic contact solution, comprising:

polyhexamethylenebiguanide HCL;

boric acid;

sodium borate;

edate disodium;

sodium chloride;

poloxamine;

tetrasodium etidronate;

hydrochloride acid;

sterile water;

citrus acid;

gluconic acid;

tartanic acid;

potassium citrate; and carbonate sodium.

3. A method for cleaning contact lenses and producing visible discharge comprising the application of composition of claim 1 to contact lenses in a container.

4. A method for cleaning contact lenses and producing visible discharge comprising the application of composition of claim 2 to contact lenses in a container.

* * * * *